US010278430B2

(12) United States Patent
Cyphert et al.

(10) Patent No.: US 10,278,430 B2
(45) Date of Patent: *May 7, 2019

(54) ELECTRONIC PIPE WITH MODIFIED HEAT SOURCE

(71) Applicant: Healthier Choices Management Corp., Hollywood, FL (US)

(72) Inventors: Gilbert Cyphert, Phoenix, AZ (US); Edwin Balder, Mesa, AZ (US); Daniel Julia, Phoenix, AZ (US)

(73) Assignee: Healthier Choices Management Corp., Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/010,727

(22) Filed: Jun. 18, 2018

(65) Prior Publication Data

US 2018/0295887 A1 Oct. 18, 2018

Related U.S. Application Data

(63) Continuation-in-part of application No. 15/603,366, filed on May 23, 2017, now Pat. No. 10,021,906, which is a continuation-in-part of application No. 13/987,851, filed on Sep. 9, 2013, now Pat. No. 9,687,025.

(60) Provisional application No. 61/743,720, filed on Sep. 10, 2012.

(51) Int. Cl.

*A24F 47/00* (2006.01)
*A61M 15/06* (2006.01)
*H05B 6/10* (2006.01)
*A24F 1/28* (2006.01)
*A24F 7/02* (2006.01)

(52) U.S. Cl.

CPC ............. *A24F 47/008* (2013.01); *A24F 1/28* (2013.01); *A24F 7/02* (2013.01); *H05B 6/105* (2013.01)

(58) Field of Classification Search

CPC ................................ A24F 47/00; A61M 15/06
See application file for complete search history.

(56) References Cited

U.S. PATENT DOCUMENTS 2,104,266 A * 1/1938 McCormick .......... A24F 47/008 131/175
4,907,606 A * 3/1990 Lilja ..................... A24B 15/18 131/194

* cited by examiner

*Primary Examiner* — Cynthia Szewczyk
(74) *Attorney, Agent, or Firm* — Berger Singerman LLP; Geoffrey Lottenberg, Esq.

(57) ABSTRACT

An electronic pipe includes a pipe section comprising an outer shell with a coil placed around and along the inside surface of the shell. The pipe section also may include a connector element coupled to a connector element on a battery section, with both connector elements structured to transmit an electric current from the battery to the coil. A material container is insertable into the pipe section such that the coil is disposed between the inside surface of the outer shell and the material container. The coil is capable of initiating a combustion reaction inside the material container.

6 Claims, 5 Drawing Sheets

ELECTRONIC PIPE WITH MODIFIED HEAT SOURCE

This application is a continuation-in-part of U.S. patent application Ser. No. 15/603,366 filed May 23, 2017, which is a continuation-in-part of U.S. patent application Ser. No. 13/987,851 filed Sep. 9, 2013, now U.S. Pat. No. 9,687,025 issued Jun. 27, 2017, which claims the benefit of U.S. Provisional Application 61/743,720 filed on Sep. 10, 2012.

FIELD OF THE INVENTION

The present invention relates to an electronic pipe.

BACKGROUND OF THE INVENTION

Despite the fact that "smoking is harmful to your health", the number of smokers worldwide is up to 1 billion, and the number is increasing every year. In 2003, the World Health Organization (WHO) concluded a global Framework Convention on Tobacco Control. According to the statistical data from WHO, about 4.9 million people die of diseases caused by smoking each year. Although smoking may cause serious respiratory diseases and cancer, it remains extremely difficult for smokers to quit smoking.

The active ingredient in a cigarette or pipe is nicotine. During smoking, nicotine, along with tar aerosol droplets produced in the cigarette when it burns, enters a smoker's alveolus and is rapidly absorbed. After being absorbed into the blood of a smoker, nicotine then produces its effect on the receptors of the smoker's central nervous system, which makes the smoker relax and enjoy an inebriety similar to that produced by an exhilarant.

Nicotine is a kind of alkaloid with a low molecular weight and its half-life in blood is quite short. The major harmful substance in tobacco is tar, which is composed of thousands of ingredients, tens of which are carcinogenic substances. It has been proven that passive smoking can be more harmful to non-smokers than smoking is to the smoker.

Some cigarette and pipe substitutes containing only nicotine without tar have been proposed, many of them, such as the "nicotine patch," "nicotine mouthwash," "nicotine chewing gum," "nicotine drinks" etc., are made of pure nicotine. Although these cigarette and pipe substitutes are free from tar, their major disadvantage is that an effective peak concentration of nicotine cannot be reached in the blood of a smoker due to slow absorption of the nicotine. In addition, these cigarette and pipe substitutes cannot satisfy the habitual smoking actions of a smoker, for example, the inhaling action and the physical manipulation of the cigarette or pipe itself.

Therefore, there remains a need to overcome one or more of the limitations in the above-described, existing art. The discussion of the background to the invention included herein is included to explain the context of the invention. This is not to be taken as an admission that any of the material referred to was published, known, or part of the common general knowledge at the priority date of the claims.

It will be recognized that some or all of the Figures are schematic representations for purposes of illustration and do not necessarily depict the actual relative sizes or locations of The elements shown. The Figures are provided for the purpose of illustrating one or more embodiments of the invention with the explicit understanding that they will not be used to limit the scope or the meaning of the claims.

DETAILED DESCRIPTION

In the following description, for the purposes of explanation, numerous specific details are set forth in order to provide a thorough understanding of the electronic pipe of the present invention. It will be apparent, however, to one skilled in the art that the electronic pipe may be practiced without some of these specific details. Throughout this description, the embodiments and examples shown should be considered as exemplars, rather than as limitations on the electronic pipe. That is, the following description provides examples, and the accompanying drawings show various examples for the purposes of illustration. However, these examples should not be construed in a limiting sense as they are merely intended to provide examples of the electronic pipe rather than to provide an exhaustive list of all possible implementations of the electronic pipe.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner in one or more embodiments.

Figure 1:
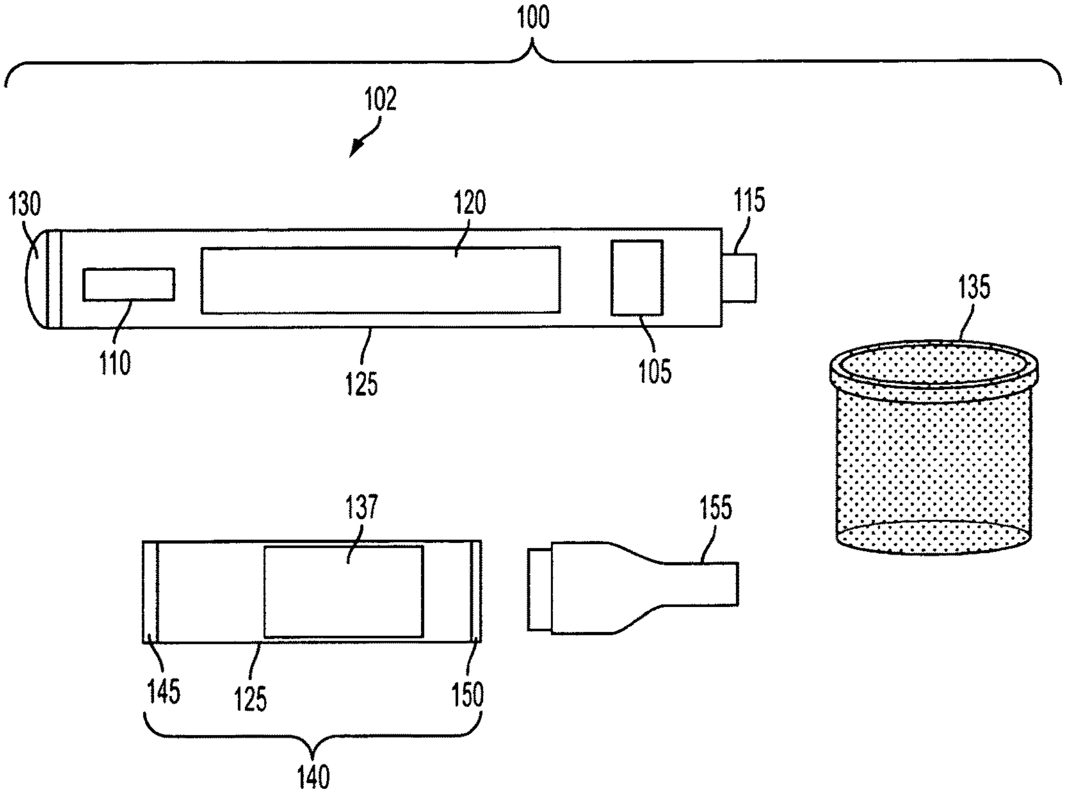
FIG. 1 is a view of a first embodiment of an electronic pipe embodying the principals of the invention.
Figure 2:
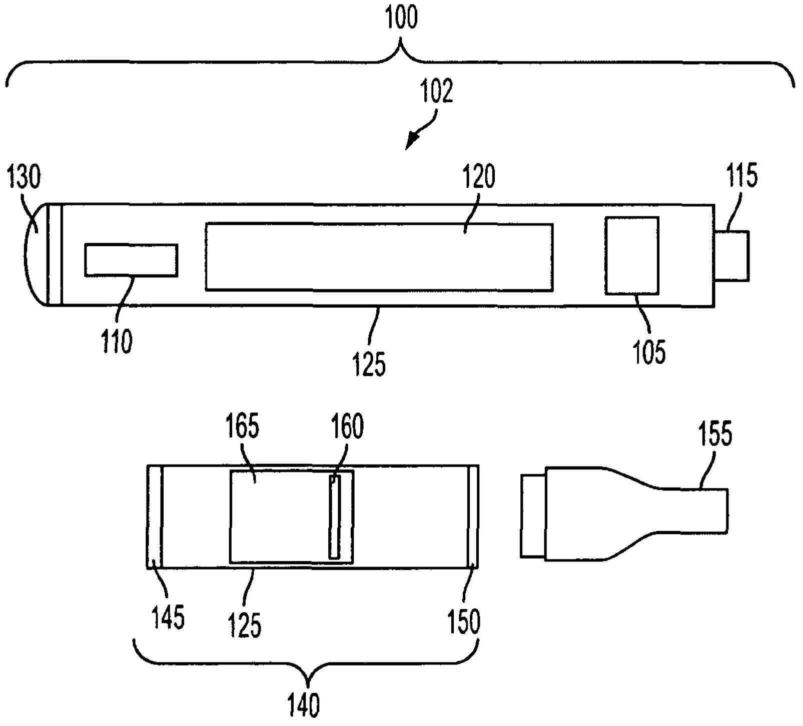
FIG. 2 is a view of a second embodiment of an electronic pipe embodying the principals of the invention.
Figure 3:
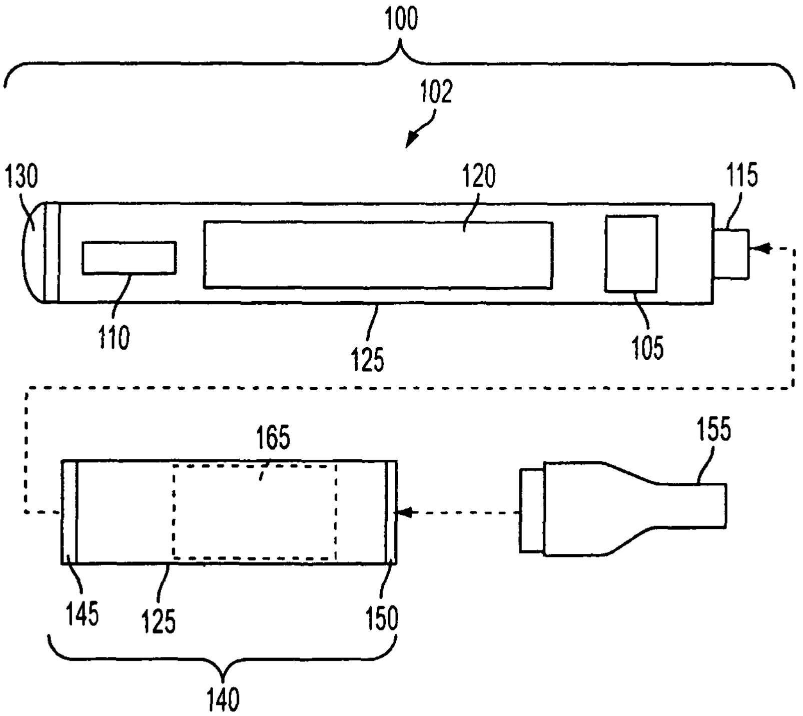
FIG. 3 is a view of a third embodiment of an electronic pipe embodying the principals of the invention.

Referring now to FIGS. 1-3, an electronic pipe 100 is illustrated. As shown in the figures, a first pipe section 102 includes a printed circuit board, or an integrated circuit, or a memory module encoded with a program (with the integrated circuit or the memory module possibly mounted on a printed circuit board) 105 located within the first pipe section 102. The printed circuit board 105 communicates with a liquid crystal display (LCD) 110 located on the first pipe section 102 so that the LCD is visible to a user. The LCD display 110 communicates with the printed circuit board 105 and a charging head 115 in the form of a male USB jack or outlet that enables the rechargeable battery 120 to be charged. In one embodiment, the rechargeable battery 120 is located within the first pipe section 102. It will be appreciated that other types of jacks, or charging heads 115 may be employed. Also, the rechargeable battery 120 may be a lithium battery or any other type of rechargeable battery.

The first pipe section includes an outer shell 125 comprised of stainless steel, but it will be appreciated that other materials may be employed, such as aluminum alloys, plastics, and a combination of the above materials. The cross-section shape of the outer shell 125 may be cylindrical, square, ellipsoidal or other desired shapes.

A light emitting diode (LED) tip indicator 130 is located on a distal end of the outer shell 125 of the first pipe section 102. Adjacent to the printed circuit board 105 is a depressible button (not shown). When pressing the button, the rechargeable battery 120 supplies power to several elements of the electronic pipe 100 as discussed below. This includes providing power to a heat source 160, a heating net 135, the LED tip indicator 130, and other components in the electronic pipe 100, as required.

As shown in FIG. 1, a heating net 135 is provided for holding and burning a combustible material such as tobacco. Once filled with tobacco, the heating net 135 is set inside a heating net receiver 137 that is located in a second pipe section 140 or on the surface of the second pipe section 140 that is detachable and re-attachable from the first pipe section 102. The second pipe section 140 includes a connector 145 at one end that enables the second pipe section 140 to be fixed or removably attachable to the charging head 115. Once connected to the charging head 115, the second pipe section 140 receives electricity from the rechargeable battery 120 to thereby heat the heating net 135. Thus, in one embodiment, the connector 145 is a matching female USB element that mates to the male USB element comprising the charging head 115.

The second pipe section 140 includes an outer shell 125 like the first pipe section 10 of the electronic pipe 100, with the outer shell 125 comprised of stainless steel, but it will be appreciated that other materials may be employed, such as aluminum alloys, plastics, and a combination of the above materials. The cross-section shape of the outer shell 125 may be cylindrical, square, ellipsoidal or other desired shapes.

The second pipe section 140 also includes a mouthpiece receiver 150 that is sized to removably receive a mouthpiece 155 that is intended for insertion into a user's mouth.

The first embodiment of the electronic pipe 100 illustrated in FIG. 1 includes several features. For example, the battery 120 is rechargeable and can be plugged into a USB or wall adaptor for charging. Also, the printed circuit board 105 includes a locking capability. When the pressable button (not shown) is pressed 3 times within 2 seconds, the rechargeable battery 120 is locked (i.e., power is unavailable to any component of the electronic pipe 100). When the pressable button (not shown) is pressed 3 times within 2 seconds, again, the rechargeable battery 120 is unlocked. This safety feature ensures that the electronic pipe 100 will not begin heating the heating net 135 when the electronic pipe 100 is located in a user's pocket or when not in use.

In addition, the printed circuit board 105 has a counting function which counts how many times a user presses the pressable button, and the count is displayed on the LCD display 110. This function is reset when the rechargeable battery 120 is recharged through plugging the USB charging head into a power source. The LCD display 110 shows the present charged state of the rechargeable battery 120. For example, when the rechargeable battery 120 is fully charged, the LCD display 110 shows 4 lines. When the rechargeable battery 120 needs to be charged, no lines are displayed on the LCD display 110. In this state, the LED tip 130 flashes 10 times to alert the user that the rechargeable battery 120 needs to be charged.

Before using the electronic pipe 100 the user loads tobacco, or any type of combustible material desired, into the heating net 135, then inserts the heating net 135 into the heating net receiver 137. Then the mouthpiece 155 is installed onto the mouthpiece receiver 150. After doing so, the connector 145 of the detachable component 140 is screwed or inserted over or into the charging head 115. Once connected to the charging head 115, the heating net receiver 137, or a heat source 160 (shown in FIG. 2) located in the heat source receiver 137 receives electricity from the rechargeable battery 120 to thereby heat the heating net 135 and ignite the combustible material located in the heating net 135. Alternatively, the removable heating net 135 may remain inside the heating net receiver 137 and be loaded with tobacco in place while the detachable component 140 is connected. The user may press the pressable button (not shown) that is on, or adjacent to the printed circuit board 105. When pressing the pressable button, the LED tip 130 illuminates, and/or alternatively, the LCD display 110 may also illuminate, thereby indicating that the rechargeable battery 120 is supplying power to the heating net receiver 137. The tobacco, or other ignitable material therein will then be ignited.

Referring now to FIG. 2, a second embodiment electronic pipe 100 is illustrated. The elements and reference numbers discussed above in connection with the embodiment illustrated in FIG. 1 apply to the embodiment illustrated in FIG. 2. Similar to the embodiment illustrated in FIG. 1, a first pipe section 102 includes a printed circuit board, or an integrated circuit, or a memory module encoded with a program (with the integrated circuit or the memory module possibly mounted on a printed circuit board) 105 located within the first pipe section 102. The printed circuit board 105 communicates with a liquid crystal display (LCD) 110 located on the first pipe section 102 so that the LCD is visible to a user. The LCD display 110 communicates with the printed circuit board 105 and a charging head 115 in the form of a male USB jack or outlet that enables the rechargeable battery 120 to be charged. In one embodiment, the rechargeable battery 120 is located within the first pipe section 102. It will be appreciated that other types of jacks, or charging heads 115 may be employed. Also, the rechargeable battery 120 may be a lithium battery or any other type of rechargeable battery.

The electronic pipe 100 shown in FIG. 2 includes an outer shell 3 comprised of stainless steel, but it will be appreciated that other materials may be employed, such as aluminum alloys, plastics, and a combination of the above materials. Again, similar to the embodiment illustrated in FIG. 1, a light emitting diode (LED) tip indicator 130 is located on a distal end of the outer shell 125 of the first pipe section 102. Adjacent to the printed circuit board 105 is a depressible button (not shown). When pressing the button, the rechargeable battery 120 supplies power to several elements of the electronic pipe 100 as discussed below. This includes providing power to a heating net 135, the LED tip indicator 130, and other components in the electronic pipe 100, as required.

In the embodiment illustrated in FIG. 2, a heat source 160 is employed for heating the tobacco, or any other desired combustible material. The heat source 160 is designed to heat to a temperature sufficient to ignite a combustible material that is placed in the combustible material reservoir 165 when an electric current is applied to the heat source 160. In some embodiments, the combustible material reservoir 165 may be located on the surface of and extends into the second pipe section 140.

In addition, a filter (not shown) designed to minimize the passage of particulate matter to the mouthpiece 155 may be included in the both of the embodiments illustrated in FIGS. 1 and 2. For example, referring to FIG. 2, the filter may be located between the 20 mouthpiece receiver 150 and the combustible material reservoir 165, or it may be located between the mouthpiece 155 and the mouthpiece receiver 150.

The heat source 160 is located in a second pipe section 140 that is detachable and re-attachable from the first pipe section 102. The second pipe section 140 includes a connector 145 at one end that enables the second pipe section 140 to be fixed or removably attachable to the charging head 115. Once connected to the charging head 115, the second pipe section 140 receives electricity from the rechargeable battery 120 to thereby heat the heat source 160. Thus, in one embodiment, the connector 145 is a matching female USB element that mates to the male USB element comprising the charging head 115.

Like the embodiment of FIG. 1, the second pipe section 140 also includes a mouthpiece receiver 150 that is sized to removably receive a mouthpiece 155 that is intended for insertion into a user's mouth. The second embodiment of the electronic pipe 100 illustrated in FIG. 2 includes several features. For example, the battery 120 is rechargeable and can be plugged into a USB or wall adaptor for charging. The printed circuit board 105 includes a locking capability. When the pressable button (not shown) is pressed 3 times within 2 seconds, the rechargeable battery 120 is locked (i.e., power is unavailable to any component of the electronic pipe 100). When the pressable button (not shown) is pressed 3 times within 2 seconds, again, the rechargeable battery 120 is unlocked. This safety feature ensures that the electronic pipe 100 will not begin heating the heating net 135 when the electronic pipe 100 is located in a user's pocket or when not in use.

In addition, the printed circuit board 105 has a counting function which counts how many times a user presses the pressable button, and the count is displayed on the LCD display 110. This function is reset when the rechargeable battery 120 is recharged through plugging the USB charging head into a power source. The LCD display 110 shows the present charged state of the rechargeable battery 120. For example, when the rechargeable battery 120 is fully charged, the LCD display 110 shows 4 lines. When the rechargeable battery 120 needs to be charged, no lines are displayed on the LCD display 110. In this state, the LED tip 130 flashes 10 times to alert the user that the rechargeable battery 120 needs to be charged.

Before using the electronic pipe 100 the user loads tobacco, or any type of combustible material desired, into the combustible material reservoir 165 that includes the heat source 160 mounted within the combustible material reservoir 165. Then the mouthpiece 155 is installed onto the mouthpiece receiver 150. After doing so, the connector 145 of the detachable component 140 is screwed or inserted over or into the charging head 115. Once connected to the charging head 115, the heat source 160 receives electricity from the rechargeable battery 120 to thereby heat the heat source 160 and ignite the combustible material located in the combustible material reservoir 165.

The user may press the pressable button (not shown) that is on, or adjacent to the printed circuit board 105. When pressing the pressable button, the LED tip 130 illuminates, and/or alternatively, the LCD display 110 may also illuminate, thereby indicating that the rechargeable battery 120 is supplying power to the heating net receiver 137. The tobacco or other ignitable material therein will then be ignited.

One feature of the second embodiment electronic pipe 100 illustrated in FIG. 2, the user simply has to load tobacco, or any other combustible material inside the combustible material reservoir 165, which eliminates the step of inserting the heating net 135, as required in the first embodiment illustrated in FIG. 1.

The printed circuit board, or chip 105 may comprise an electronic assembly that allows communication between the various components discussed above. For example, in one embodiment, the printed circuit board, or chip 105 may comprise an embedded data processor connected via an internal bus to a read only memory containing the executable code for causing the microprocessor to perform the functions described herein. In another embodiment, the printed circuit board, or chip may comprise one or more electronic circuits that employ one or more switches to perform the functions described herein.

Referring now to FIG. 3, a third embodiment electronic pipe 100 is illustrated. The features, elements and reference numbers discussed above in connection with FIGS. 1 and 2 apply to the embodiment illustrated in FIG. 3. As shown in FIG. 3, the combustible material reservoir 165 is located within the second pipe section 140. That is, in one embodiment, the second pipe section 140 has a circular cross-section, with an aperture, or opening at the mouthpiece receiver 150 sized to receive both the mouthpiece 155 and a combustible material that is placed into the second pipe section 140 before the mouthpiece 155 is placed over the mouthpiece receiver 150. In this embodiment, only a small hole, or aperture (not shown) is located in the second pipe section 140 so that air can be provided to the combustible material reservoir 165, which is positioned entirely within the second pipe section 140.

One feature of this embodiment is that the combustible material cannot "spill" from an exterior opening. The only way to insert or remove the combustible material is to remove the mouthpiece 155, and access the combustible material reservoir 135 from the opening located at the mouthpiece receiver 150.

In all of the embodiments illustrated in FIGS. 1-3, a passageway to permit air to flow between the mouthpiece receiver 150 and the heating net receiver 137 (in FIG. 1) or the combustible material reservoir 165 (in FIGS. 2-3) is located within the second pipe section 140.

As noted herein, in some embodiment the first pipe section 102 and the second pipe section 140 may be separate, removably attachable components. However, in some embodiments the first pipe section 102 and the second pipe section 140 are fixed to one another and integrated into a "one piece" embodiment.

Figure 4:
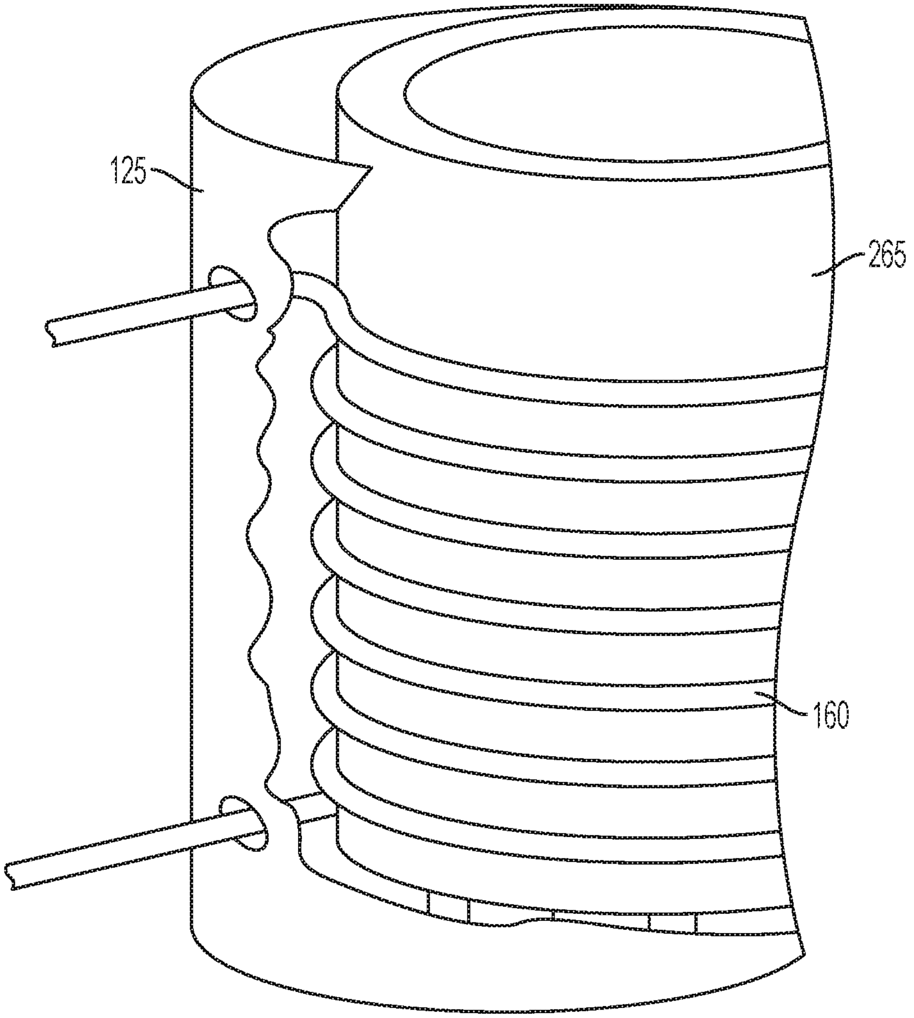
FIG. 4 is a schematic of the heat source configured as coil heater.

With reference to FIG. 4, shown is the heat source 160 configured as a coil in use in combination with a cup-type or tube-type material container 265 such as that described in Applicant's U.S. patent application Ser. No. 15/832,582, filed Dec. 5, 2017; Ser. No. 15/885,614, filed Jan. 31, 2018; and Ser. No. 15/908,304, filed Feb. 28, 2018, each of which is incorporated by reference herein in its entirety. Here, heat source 160 comprises a wire coil disposed inside an outer shell 125 of the pipe or a section thereof such as, for example, second section 140. The coil 160 is disposed concentrically with respect the outer shell 125 and, in some embodiments, is helically coiled around and along the inside surface of thereof. A removable and insertable material container 265 inserted into the outer shell 125, inside the coil 160, such that the coil 160 is disposed around the outer surface of the container 265. The container 265 is analogous to the heating net 135 and is inserted into the space delimited by the coil 160, such space analogous to the heating net receiver 137 in other embodiments. Notably, however, in some embodiments container 265 comprises a quartz, glass, silica, or other semi-precious gem material as described in the above referenced and incorporated applications.

Accordingly, the coil 160 is disposed between the outer shell 125 and the outer surface of the container 265. The coil 160 is in electrical communication with the battery 120 such that upon transmission of power the coil 160 generates heat. In some embodiments the heat is sufficient to initiate a combustion reaction and ignite the combustible material contained in the container 265. It is noted that in some embodiments the density of the reservoir 165 (or net 135) should be minimized so that optimal temperature is reached more quickly and cool down of the system components is achieved more quickly. It is additionally noted that the structural configuration promotes indirect heating and combustion of the target combustible material as the combustible material is not brought in direct contact with the heat source, i.e. coil 160. Rather, the coil 160 heats the container 265 which thereby heats the combustible material inside the container. Thus, the combustible material is indirectly heated by the coil 160. This promotes a reduction in toxins present in the inhalant produced by the heating action as described in Applicant's applications heretofore incorporated by reference.

Figure 5A:
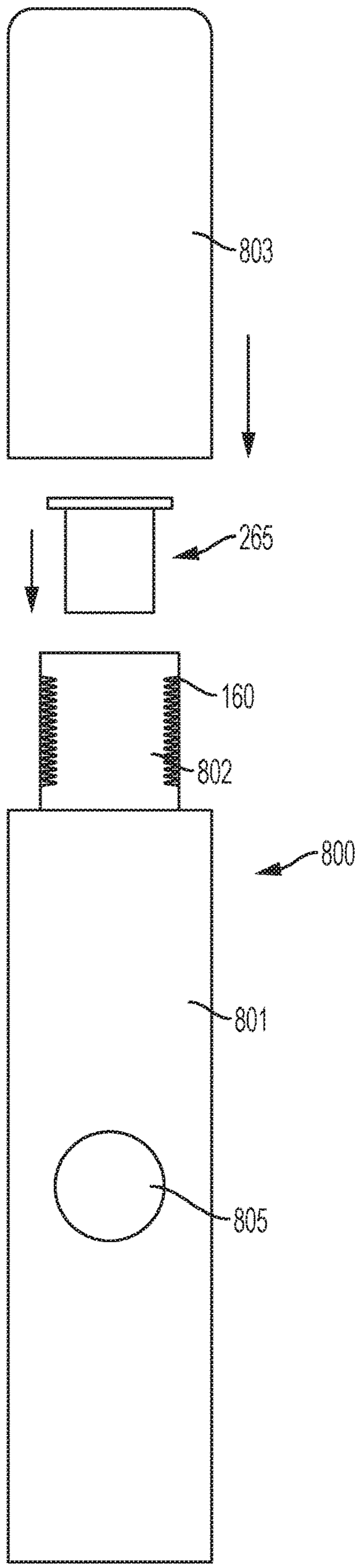
FIG. 5A is an exploded view of one embodiment of an electronic smoking device using the coil heater.
Figure 5B:
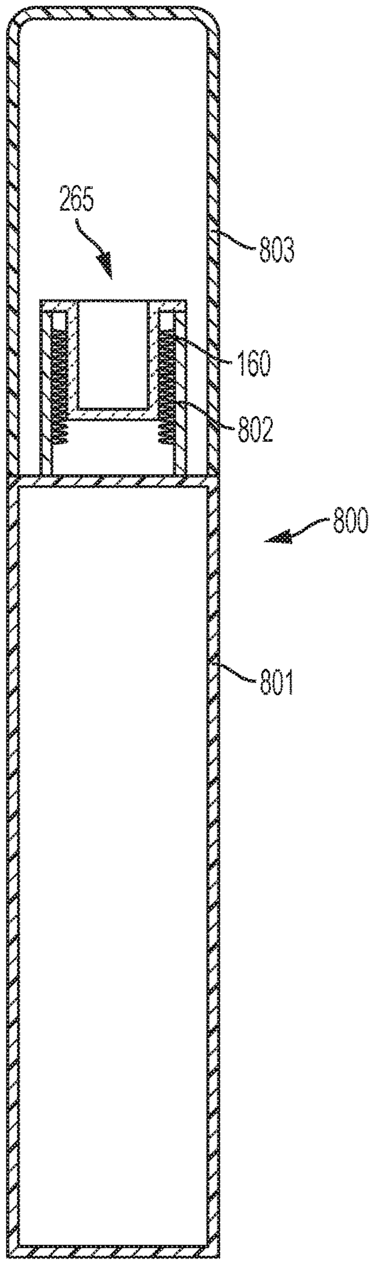
FIG. 5B is an assembled view of one embodiment of an electronic smoking device using the coil heater.

With reference to FIGS. 5A and 5B, shown is an exemplary electronic smoking device 800. It is appreciated and understood that the coil 160 is configured to be used with a plurality of types of electronic smoking devices and apparatuses including without limitation the embodiments shown in FIGS. 1-3 herein as well as that shown in FIGS. 5A and 5B. Accordingly, its use is not limited in application to the specific electronic smoking device and is rather modular to be used with a variety of such devices. The configuration of smoking device 800 is for exemplary purposes only, but in this case comprises a multi-component modular-type vaporizer that includes a control section 801, a heating chamber 802, and a removable mouthpiece 803. The control section 801 comprises a battery and chipset to control the device 800. The heating chamber 802 is analogous to the second section 140 described in other embodiments herein and is shown as open topped cup-like device delimited by an outer shell and includes a heat source, i.e. coil 160 disposed therein. In some embodiments, the heating chamber 802 is removably and threadingly engaged with the control section 801 to provide a physical and electrical connection. In some embodiments, the mouthpiece 803, heating chamber 802 and/or the control section 801 include external apertures and air passages to allow for the passage of air through the system in order to draw vapor, smoke, or aerosol therethrough.

Traditionally, in these types of units, the inhalant material is to be manually inserted into the heating chamber 802 such that it comes in direct contact with the heating element 804 and the inside of the heating chamber 802. This direct contact, which causes a toxic reaction and build-up inside the heating chamber 802, is obviated by the container 265. Accordingly, the container 265 is configured and dimensioned to be inserted into and removably retained by the heating chamber 802. In some embodiments, the container 265 fits security inside coil 160 of the heating chamber 802 by way of an interference fit. This puts the outer surface of the container 265 in close proximity or in direct contact with the coil 160. In other words, the coil 160 at least partially surrounds the container 265 or is "coiled around" the container 265. In some embodiments, after the container 10 is loaded into the heating chamber 802, the mouthpiece 803 is disposed over the area surrounding the heating chamber 802 and snaps onto or is otherwise secured to the control section 801.

In use, the user activates the device 800, typically by a control button 805, which applies electrical current to the coil 160, which generates heat. Heat generated by the coil 160 passes through the container 265 and thereby heats the inhalant material, i.e. combustible material, held in the internal storage area 14. The material then turns into a vapor, smoke, or aerosol to be inhaled by the user through air passages within the device and out of the mouthpiece 803. In some embodiments, combustion occurs as noted throughout this disclosure. Notably, air passes through the device 800 components and through the container 265 such that the vapor, smoke, or aerosol is released and pulled out of the open top of the container 265 and through and out of the mouthpiece 803. Once the inhalant material has been exhausted from the container 265, the container 265 can be removed and replaced for the next session.

The use of the container 265 avoids any direct contact between the inhalant material and the coil 160 thereby preventing a toxic reaction and preventing residue from building up on the coil 160 and within the heating chamber 802. The container 265 is easily replaced for the next use, while the heating element remains clean and unobstructed. Moreover, the use of the coil 160, which is in some embodiments, provides even exposure of the side walls of the container 265 to the surface area of the coil 160, results in a more even and efficient thermal reaction as compared to units that heat solely from the bottom or the top of the container 265. Heating from the sides also can mitigate excess heat or boiling over that can occur from top-down or bottom-up heating configurations.

It is further appreciated and understood that the electronic pipe disclosed herein is configured to combust a variety of types of combustible material including without limitation dry herb, tobacco, herbal concentrates, medical concentrates, wax-based concentrates, and oil-based concentrates provided a combustion reaction is desired to release associated chemical, medicaments, and substances from same.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise. Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means. The enumerated listing of items does not imply that any or all of the items are mutually exclusive, unless expressly specified otherwise. The terms "a", "an" and "the" mean "one or more", unless expressly specified otherwise. Elements of the invention that are in communication with each other need not be in continuous communication with each other, unless expressly specified otherwise. In addition, elements of the invention that are in communication with each other may communicate directly or indirectly through one or more other elements or other intermediaries.

Thus, it is seen that electronic pipe with a modified laser or induction heat source is provided. One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

The invention claimed is:

1. An electronic pipe, comprising:

a first pipe section comprising a battery, an electronic module and a first connector element, the battery and first connector element both communicating with the electronic module;

a second pipe section comprising:

an outer shell;

a second connector element coupled to the first connector element, with both connector elements structured to transmit an electric current from the battery to a heat source;

the heat source comprising a coil disposed around and along an inside surface of the outer shell; and the heat source initiating a combustion reaction in the second pipe section.

2. The electronic pipe of claim 1, including a removable material container inserted into the second pipe section such that said coil is disposed between the outer shell and the material container.

3. The electronic pipe of claim 2, wherein the material container is a tube.

4. The electronic pipe of claim 2, wherein the material container is a cup.

5. The electronic pipe of claim 1, further comprising a mouthpiece structured to be removably attachable to the mouthpiece receiver.

6. The electronic pipe of claim 1, where the electronic module is selected from a group consisting of: a printed circuit board, an integrated circuit, a computer chip; a printed circuit board having an integrated circuit mounted thereon, and a memory module encoded with a program.

* * * * *